United States Patent [19]

Chung

[11] 4,414,971
[45] Nov. 15, 1983

[54] SANITARY PANTS USED FOR THE MALE

[76] Inventor: Seun Y. Chung, 309-1, Da, Shi Heung Dong, Yeung Deung Po-Ku, Seoul, Rep. of Korea

[21] Appl. No.: 269,745

[22] Filed: Jun. 2, 1981

[51] Int. Cl.³ .............................................. A61F 5/40
[52] U.S. Cl. ........................................ 128/159; 2/405
[58] Field of Search .......................... 2/405, 403, 404; 128/159

[56] References Cited

U.S. PATENT DOCUMENTS

| 2,457,260 | 12/1948 | Morris | 128/159 |
| 2,601,602 | 6/1952 | Firsching | 128/159 |

FOREIGN PATENT DOCUMENTS

| 1014066 | 8/1952 | France | 2/405 |
| 76166 | 1/1950 | Norway | 2/405 |
| 280164 | 4/1952 | Switzerland | 2/405 |
| 585841 | 2/1947 | United Kingdom | 2/405 |

Primary Examiner—H. Hampton Hunter
Attorney, Agent, or Firm—Birch, Stewart, Kolasch & Birch

[57] ABSTRACT

Sanitary underpants for the male which provide effective ventilation and absorption, said pants having a front and rear portion, said front portion being provided with a centrally disposed hole, and an exterior cloth fastened to said front portion in the vicinity of the waist and extending in the downward direction and fastened to said front portion below the hole, said exterior cloth having an expandable construction which forms with said front portion a compartment having open lateral side portions, whereby the genitals of the male are adapted to extend through said hole and be received by said compartment, thereby separating said genitals from contiguous body parts.

5 Claims, 5 Drawing Figures

SANITARY PANTS USED FOR THE MALE

BACKGROUND AND SUMMARY OF THE INVENTION

The present invention relates to pants, particularly to sanitary pants used for the male.

Generally speaking, it has been recognized that bacteria are produced by the secretions of sweat and the like which are excreted from parts of the human body which are in contact with other parts of the human body. More specifically, the peripheral portions of the testicles of the male are high areas of secreted sweat because they are in contact with the groin at all times. The secretions are caused by one's own body temperature, particularly in areas where circulation of air is very bad and where the skin is soft. When the skin becomes infected medical treatment thereof is very difficult.

Therefore, recognizing the fact that keeping one's body clean is highly desirable, there are certain situations and circumstances, for example, one's occupation, which makes it difficult to restrain the growth and the propagation of bacteria encouraged by the presence of sweat excreted from the skin and absorbed by underwear.

Customarily, underwear has been made by cotton yarn which absorbs the fine moisture. However, underpants made with cotton does not thoroughly absorb sweat and the like excreted from the vicinity of testicles. All improvements up to now have been directed to only strengthening the absorptive power of the cotton fabrics themself and to strengthen the elasticity of the belt. At present, there have not been provided any pants which have a structure for absorbing sweat and the like in the circumferential area of the groin where bacteria tends to propagate.

Accordingly, an object of the present invention is to eliminate the defects in pants customarily used by the male and to provide new and improved male underpants which are sanitary in nature and thus reduce the tendency of bacteria to develop.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

According to the present invention, a portion of the pants is inserted between the groin and the testicles so as to prevent the mutual touching of these body parts whereby the propagation of bacteria is inhibited. Thus due to absorption, these areas are maintained in a dry state and thus the secretion of sweat and the like excreted from these areas is eliminated.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

BRIEF DESCRIPTION OF THE PREFERRED EMBODIMENTS

Figure 1:
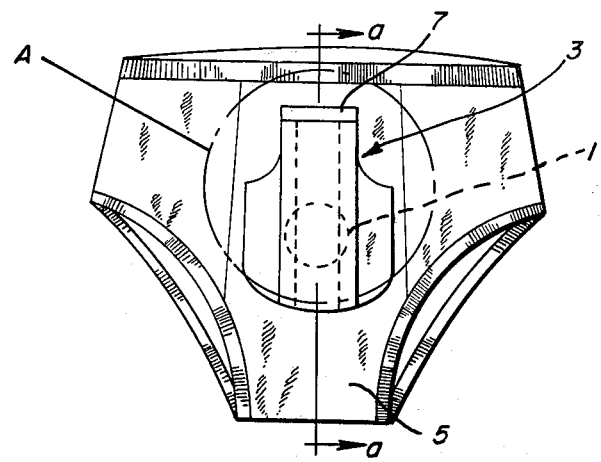
FIG. 1 is a front view of the present invention.
Figure 2:
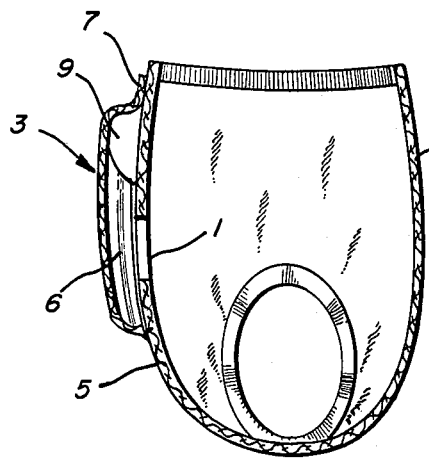
FIG. 2 is a side section taken along line a—a of FIG. 1.
Figure 3:
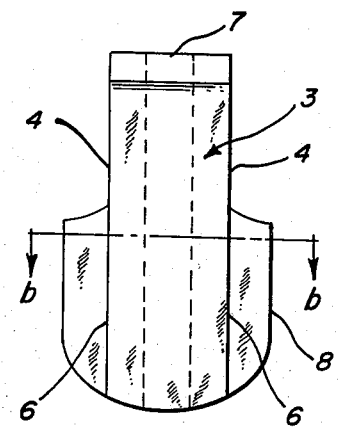
FIG. 3 is an enlarged front view of the principal part (A) of the present invention.
Figure 4:
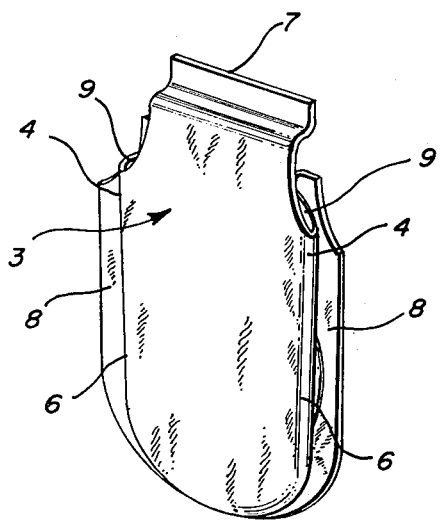
FIG. 4 is a perspective view of FIG. 3.
Figure 5:
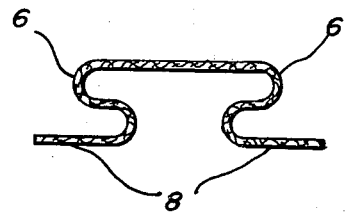
FIG. 5 is a section taken along line b—b of FIG. 3.

As shown in FIG. 1, a hole is provided in the interior portion 5 of the main-body 2 and an exterior cloth 3 is provided over the interior portion. The exterior portion 3 is made in the shape of a sack which is expanded in the downward direction and is reduced in its upward direction at the outside portion of the hole 1. The circumference of the expanded portion 8 is sewn to the main-body 2 and the top 7 of the reduced portion 4 is also sewn to the main-body 2. However, at the top of the reduced portion 4, both of the side portions are open protruding a fly and vent opening 9. Also, a pleated portion 6 is provided for expanding the volume on the inside of the expanded lower portion. Consequently, the front of the main-body 2 is formed together with an exterior cloth 3, an interior cloth 5, and a hole 1.

The effect of the pants of the present invention formed in the above manner is as follows.

When the male is wearing the pants of the present invention, the male genitals, that is, the penis and the testicles of wearer is introduced through the hole 1 and inserted into the compartment defined by the exterior cloth 3 and the interior cloth 5; thus, the male genitals are isolated from the groin and are disposed in a compartment which can be expanded and enlarged by utilizing the pleated portion 6. Because of this arrangement, the secretions excreted from the vicinity of the groin are effectively absorbed because the male genitals are completely isolated from the groin by the interior cloth 5 and the exterior cloth 3.

Also, if the wearer is prone to move quickly in varying directions, the male genitals are maintained in their original position relative to other body parts; and the wearer always feels pleasant because of the ventilation and absorption provided between the male genitals and other body parts.

The sanitary pants of the present invention provide necessary ventilation and absorption which inhibit the growth and the propagation of bacteria, thereby achieving advantageous sanitary results.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. Sanitary underpants for the male which provide effective ventilation and absorption, said pants having a front and rear portion, said front portion being provided with a centrally disposed hole, and a unitary exterior cloth fastened to said front portion in the vicinity of the waist and along the sides thereof for surrounding said hole and forming a pouch, said exterior cloth being fastened along the lateral sides thereof to said front portion up to a location just above said hole to form said pouch with said front portion, whereby the genitals of the male are adapted to extend through said hole and be received by said pouch thereby separating said genitals from contiguous body parts, said exterior cloth including side panels which have a pleated expandable configuration for permitting said pouch to be expanded, and said lateral sides of said exterior cloth being unfastened from said location just above said hole up to said vicinity of the waist to provide a vent opening between said exterior cloth and said front portion.

2. The sanitary underpants of claim 1, wherein the exterior cloth enlarges from a smaller dimension at the top of the pants to a larger dimension at the bottom of the pants.

3. The sanitary underpants of claim 2, wherein the larger dimension of the exterior cloth is provided with said expandable configuration.

4. The sanitary underpants of claim 2, wherein said exterior cloth includes a smaller dimensional portion extending from the top of the pants downward to about said location just above said hole and a larger dimensional portion extending downward from about said location just above said hole and wherein the lateral sides of said larger dimensional portion are fastened to said front portion to form said compartment and the lateral sides of said smaller dimensional portion are unattached to provide said vent opening.

5. Sanitary pants for the male which provide effective ventilation and absorption, said pants having a front and rear portion, said front portion being provided with a substantially centrally disposed hole, and a unitary exterior cloth fastened to said front portion in the vicinity of the waist and along the sides thereof for surrounding said hole and forming a pouch, said exterior cloth being fastened along the lateral sides thereof to said front portion up to a location just above said hole to form said pouch with said front portion, whereby the genitals of the male are adapted to extend through said hole and be received by said pouch to thereby separate said genitals from contiguous body parts, said exterior cloth including pre-formed pleated side panels which have a pleated expandable configuration for permitting said pouch to be expanded, and said lateral sides of said exterior cloth being unfastened from said location just above said hole up to said vicinity of the waist to provide a vent opening between said exterior cloth and said front portion.

* * * * *